(12) United States Patent
Saxena et al.

(10) Patent No.: US 7,943,794 B2
(45) Date of Patent: May 17, 2011

(54) PROCESSES FOR THE PREPARATION OF INTERMEDIATES OF VALSARTAN

(75) Inventors: Ira Saxena, Ghaziabad (IN); Asok Nath, Gurgaon (IN); Mohan Prasad, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 12/370,249

(22) Filed: Feb. 12, 2009

(65) Prior Publication Data

US 2009/0203921 A1 Aug. 13, 2009

(30) Foreign Application Priority Data

Feb. 13, 2008 (IN) .............................. 377/DEL/2008

(51) Int. Cl.
*C07C 255/50* (2006.01)

(52) U.S. Cl. ....................................... 558/414

(58) Field of Classification Search .................. 548/253; 558/414

See application file for complete search history.

(56) References Cited

U.S. PATENT DOCUMENTS

| 5,399,578 | A | 3/1995 | Bühlmayer et al. |
| 6,271,375 | B1 | 8/2001 | Villa et al. |
| 2006/0069268 | A1 | 3/2006 | Denni-Dischert et al. |
| 2006/0100443 | A1 | 5/2006 | Parthasaradhi Reddy et al. |
| 2006/0281801 | A1 | 12/2006 | Kumar et al. |

FOREIGN PATENT DOCUMENTS

WO WO 2005/049587 6/2005
WO WO 2005/049588 6/2005

OTHER PUBLICATIONS

Beutler, et al., "A High-Throughput Process for Valsartan", *Organic Process Research & Development*, 11(5), 892-898 (2007).

*Primary Examiner* — Kamal A Saeed
*Assistant Examiner* — Kristin Bianchi

(57) ABSTRACT

The present invention relates to processes for the preparation of intermediates of valsartan.

14 Claims, No Drawings

PROCESSES FOR THE PREPARATION OF INTERMEDIATES OF VALSARTAN

FIELD OF THE INVENTION

The present invention relates to processes for the preparation of intermediates of valsartan.

BACKGROUND OF THE INVENTION

Valsartan is chemically described as (S)—N-(1-carboxy-2-methylprop-1-yl)N-pentanoyl-N-[2'-(1H-tetrazol-5-yl)-biphenyl-4-ylmethyl]amine of Formula I.

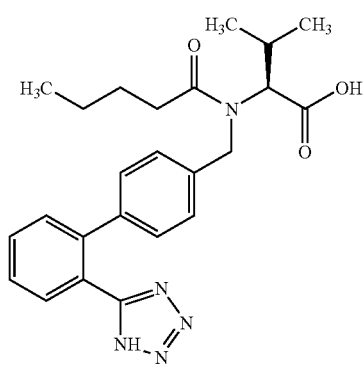

FORMULA I

Valsartan is an angiotensin II antagonist acting on the $AT_1$ receptor subtype. It is useful for the prophylaxis and treatment of diseases or conditions which may be inhibited by blocking the $AT_1$ receptor, such as high blood pressure and cardiac insufficiency.

Processes for the synthesis of valsartan and its intermediates are provided in, for example, U.S. Pat. Nos. 5,399,578 and 6,271,375, U.S. Patent Application Publication Nos. 2006/0069268, and 2006/0100443 and Org. Process Res. Dev., 2007, 11(5) 892-898.

The compounds of Formula II and Formula VI are intermediates for the preparation of valsartan.

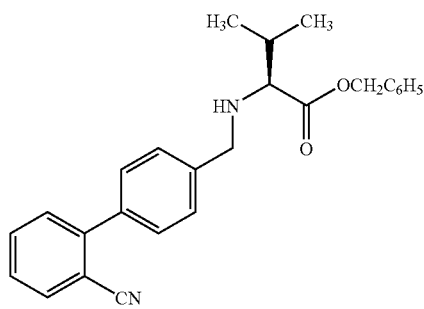

FORMULA II

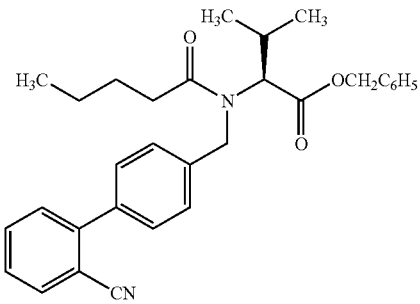

FORMULA VI

U.S. Pat. No. 5,399,578 provides a process for the preparation of the compound of Formula II by reacting a compound of Formula III

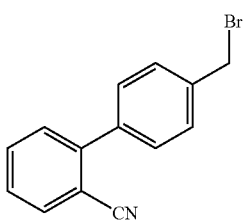

FORMULA III with the tosylate salt of Formula IV

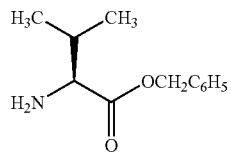

FORMULA IV in dimethylformamide in the presence of diisopropylethylamine. The reaction is carried out by stirring the reaction mixture at 80° C. for 1 hour. The compound of Formula II is further reacted with a compound of Formula V

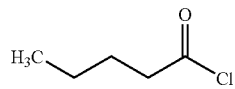

FORMULA V in methylene chloride in the presence of diisopropylethylamine to obtain the compound of Formula VI. The reaction is carried out by stirring the reaction mixture at room temperature for 20 to 25 hours. The compound of Formula VI is finally reacted with tributyltin azide and deprotected to obtain valsartan.

U.S. Patent Application Publication No. 2006/0281801 provides a process for the preparation of the compound of Formula II by reacting the compound of Formula III and the tosylate salt of Formula IV in a solvent system containing toluene or xylene and water. The reaction is carried out by heating the reaction mixture to 50° to 55° C. for 25 hours in the presence of potassium carbonate and tetrabutylammonium bromide followed by acidification with hydrochloric acid to obtain the compound of Formula II as a hydrochloride salt with 97% purity. The hydrochloride salt of the compound of Formula II is converted to its free base form by treating with aqueous sodium bicarbonate in toluene. The compound of Formula II obtained as a free base is reacted with the compound of Formula V in toluene in the presence of diisopropylethylamine at 20° C. for 30 minutes to obtain the compound of Formula VI. The compound of Formula VI is isolated with 96% purity after acid-base treatments and layer separation.

Org. Process Res. Dev., 2007, 11(5) 892-898 discloses that the use of diisopropylethylamine in the preparation of compounds of Formula II and Formula VI leads to the formation of byproducts, including (S)-3-methyl-2-pentanoylaminobutyric acid benzyl ester of Formula VII and pentanoic acid anhydride of Formula VIII in 5 to 8 mol % each.

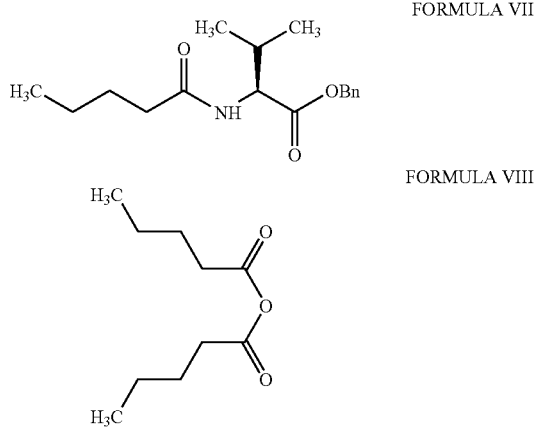

FORMULA VII

FORMULA VIII

The Org. Process Res. Dev. reference further provides a process for the preparation of compounds of Formula II and Formula VI without using diisopropylethylamine. According to this process, the compound of Formula II is prepared by reacting the compound of Formula III with the free base form of the compound of Formula IV in xylene at 60° C. for 2 hours. The compound of Formula II is isolated as a hydrochloride salt from xylene solution by the addition of aqueous hydrochloric acid at 72° C. under vigorous stirring for 2 hours and by removing the water continuously by Dean-Stark distillation. The hydrochloride salt of the compound of Formula II is further converted into its free base form by stirring at 50° C. for 30 minutes in the presence of sodium hydroxide, water and xylene. The compound of Formula II obtained as a free base is reacted with the compound of Formula V in xylene in the presence of aqueous sodium hydroxide at 40° C. for 2 hours to obtain the compound of Formula VI. The compound of Formula VI is isolated by treating with ammonia solution, layer separation and distillation.

The processes provided in the Org. Process Res. Dev. reference for preparing the compounds of Formula II and Formula VI involve the use of high-boiling solvents like xylene or toluene. U.S. Patent Application Publication No. 2006/0281801 also involves the use of xylene or toluene for the preparation of the compound of Formula II. The use of high-boiling solvents requires high temperature conditions for the reaction. Carrying out these reactions at temperature conditions above 40° C. is likely to result into degradation of the products and requires employing further purification steps, which are lengthy and uneconomical. The processes provided in Org. Process Res. Dev. also require additional steps of converting the salt forms of the compounds for Formula IV and Formula II into their free base forms prior to further reactions. The processes provided in U.S. Pat. No. 5,399,578 and U.S. Patent Application Publication No. 2006/0281801 involve the use of diisopropylethylamine, which is reported to lead to the formation of impurities.

SUMMARY OF THE INVENTION

The present inventors have developed processes for the preparation of the compounds of Formula II and Formula VI by using a phase transfer catalyst, whereby the problems associated with the prior art methods are avoided. Higher temperature conditions are not needed for the present processes and the entire reaction of obtaining the compounds of Formula II and Formula VI can be carried out at temperatures below 40° C. The use of diisopropylethylamine is also avoided in the present processes, thereby minimizing the chances of formation of (S)-3-methyl-2-pentanoylamino-butyric acid benzyl ester of Formula VII and pentanoic acid anhydride of Formula VIII. The present processes also do not require any separate step of converting the salts of Formula IV and Formula II into their free base forms prior to further reactions. Thus, the present invention substantially minimizes the formation of byproducts, avoids the necessity of employing any additional purification or process steps, and provides valsartan with higher purity. The present process is also suitable for preparing valsartan at industrial scale.

DETAILED DESCRIPTION OF THE INVENTION

In a first aspect, processes are provided for preparing the compound of Formula II having purity of about 98.0% or above, or its salts,

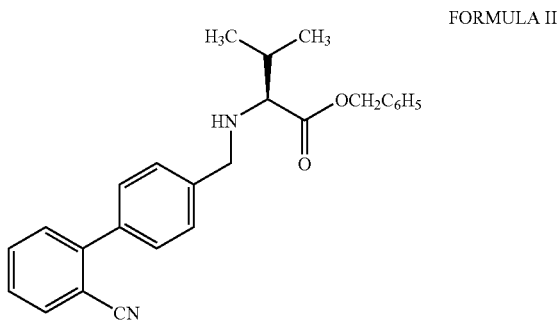

FORMULA II comprising reacting the compound of Formula III

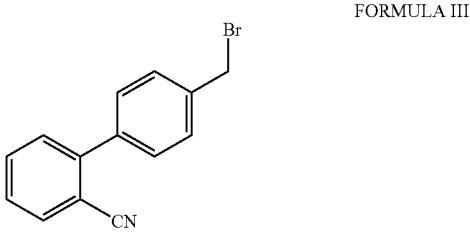

FORMULA III with the compound of Formula IV or its salt

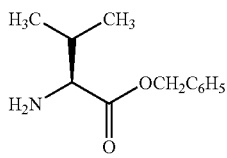

FORMULA IV in the presence of a phase transfer catalyst.

The compounds of Formula III and Formula IV may be prepared by methods, for example, by those known in the prior art, for example Org. Process Res. Dev., 2007, 11(5) 892-898. The compound of Formula IV may be used as a free base or in the form of its salt, for example, the tosylate salt.

The reaction of the compound of Formula III and the compound of Formula IV or its salt may be carried out in the presence of a solvent system comprising water and one or more water-immiscible organic solvents. Examples of water-immiscible organic solvents include halogenated hydrocarbons, esters, ethers and mixtures thereof. Examples of halogenated hydrocarbons include dichloromethane, ethylene dichloride, chloroform and mixtures thereof. Examples of esters include ethyl acetate, isopropyl acetate and mixtures thereof. Examples of ethers include diethylether, diisopropylether and mixtures thereof. The solvent system can be, for example, a mixture of water and a halogenated hydrocarbon, for example, dichloromethane.

The reaction may be carried out in the presence of a base. The base may be an inorganic base. Examples of inorganic base include alkali metal carbonates, bicarbonates, hydroxides and mixtures thereof. Examples of alkali metal carbonates include lithium carbonate, sodium carbonate and potassium carbonate. Examples of alkali metal bicarbonates include sodium bicarbonate and potassium bicarbonate. Examples of alkali metal hydroxides include sodium hydroxide and potassium hydroxide. In some embodiments, potassium carbonate is used as the base.

The phase transfer catalyst employed in the reaction of the compound of Formula III with the compound of Formula IV or its salt may be selected from, for example, tetrabutylammonium bromide, tetrapropylammonium bromide, tributylbenzylammonium chloride, tetraethylammonium bromide, tetraoctylammonium bromide, tetrabutylammonium hydrogen sulfate, benzyltrimethylammonium chloride, benzyltriethylammonium chloride, tetrabutylammonium acetate, tetrabutylammonium iodide, ethyltriphenylphosphonium bromide, and ethyltriphenylphosphonium iodide. In some embodiments, tetrabutylammonium bromide may be used as the phase transfer catalyst.

The reaction may be carried out at a temperature below about 40° C., for example, at about −20° to about 35° C. The reaction may be facilitated by stirring the reaction mixture for up to about 30 hours, for example, about 15 hours to about 25 hours. The compound of Formula II is obtained with a purity of about 98.0% or above, for example, with a purity of about 99.0% or above, or for example, with a purity of about 99.5% or above.

The compound of Formula II may be isolated as a free base or as a salt from the reaction mixture. The compound of Formula II may be isolated, for example, as an acid addition salt by treating the reaction mixture with an acid, for example, hydrochloric acid. The isolation of the compound of Formula II or its salts may be performed by the methods including layer separation, concentration, precipitation, filtration, decantation, distillation or a combination thereof.

In a further aspect, processes for preparing the compound of Formula VI are provided

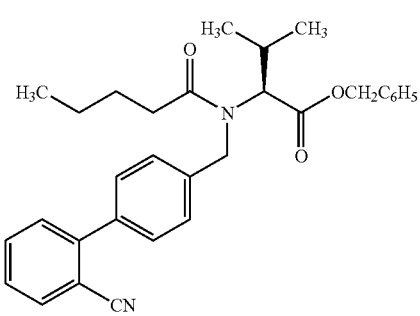

FORMULA VI comprising reacting the compound of Formula II or its salt

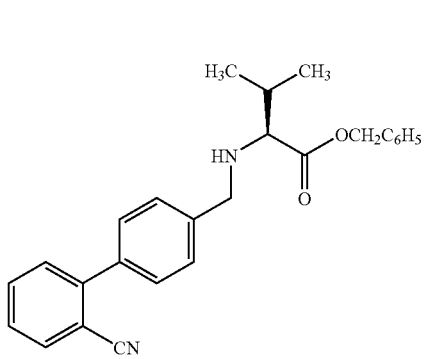

FORMULA II with the compound of Formula V

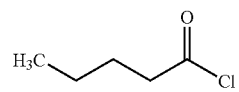

FORMULA V in the presence of a phase transfer catalyst

The compound of Formula II or its salt may be prepared as described above or by methods known in the prior art, for example Org. Process Res. Dev., 2007, 11(5) 892-898. The compound of Formula II may be used as a free base or in the form of its salt, for example, the hydrochloride salt.

The reaction of the compound of Formula II or its salt and the compound of Formula V may be carried out in the presence of a solvent system comprising water and one or more water-immiscible organic solvents. Examples of water-immiscible organic solvents include halogenated hydrocarbons, esters, ethers and mixtures thereof. Examples of halogenated hydrocarbons include dichloromethane, ethylene dichloride, chloroform and mixtures thereof. Examples of esters include ethyl acetate, isopropyl acetate and mixtures thereof. Examples of ethers include diethylether, diisopropylether and mixtures thereof. The solvent system can be, for example, a mixture of water and a halogenated hydrocarbon, for example, dichloromethane.

The reaction may be carried out in the presence of a base. The base may be an inorganic base. Examples of inorganic base include alkali metal carbonates, bicarbonates, hydroxides and mixtures thereof. Examples of alkali metal carbonates include lithium carbonate, sodium carbonate and potassium carbonate. Examples of alkali metal bicarbonates include sodium bicarbonate and potassium bicarbonate. Examples of alkali metal hydroxides include sodium hydroxide and potassium hydroxide. In some embodiments, potassium carbonate is used as the base.

The phase transfer catalyst employed in the reaction of the compound of Formula II or its salt with the compound of Formula V may be selected from, for example, tetrabutylammonium bromide, tetrapropylammonium bromide, tributylbenzylammonium chloride, tetraethylammonium bromide, tetraoctylammonium bromide, tetrabutylammonium hydrogen sulfate, benzyltrimethylammonium chloride, benzyltriethylammonium chloride, tetrabutylammonium acetate, tetrabutylammonium iodide, ethyltriphenylphosphonium bromide, and ethyltriphenylphosphonium iodide. In some embodiments, tetrabutylammonium bromide may be used as the phase transfer catalyst.

The reaction may be carried out at a temperature below about 40° C., for example, at about −20° to about 35° C. For example, the reaction may be carried out at about −10° to about 5° C. The reaction may be facilitated by stirring the reaction mixture for up to about 30 hours, for example, about 30 minutes to about 5 hours.

The compound of Formula VI may be isolated from the reaction mixture or used in the subsequent steps of preparing valsartan without isolation. The isolation of the compound of Formula VI, if desired, may be carried out by the methods including layer separation, concentration, precipitation, filtration, decantation, distillation or a combination thereof.

In another aspect, processes for preparing the compound of Formula VI are provided

FORMULA VI comprising the steps of:
a) reacting the compound of Formula III

FORMULA III with the compound of Formula IV or its salt

FORMULA IV in the presence of a phase transfer catalyst to obtain the compound of Formula II or its salt, and

FORMULA II b) reacting the compound of Formula II or its salt with the compound of Formula V

FORMULA V in the presence of a phase transfer catalyst to obtain the compound of Formula VI.

In a still further aspect, processes for preparing the compound of Formula VI are provided

FORMULA VI comprising the steps of:
a) reacting the compound of Formula III

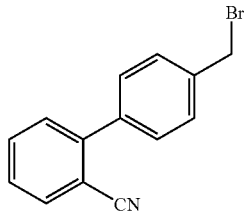

FORMULA III with the compound of Formula IV or its salt

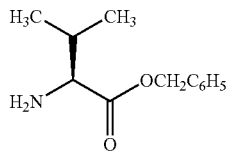

FORMULA IV to obtain the compound of Formula II or its salt, and

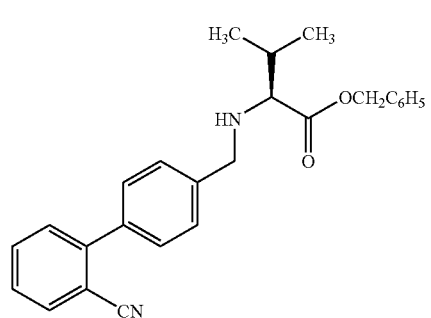

FORMULA II b) reacting the compound of Formula II or its salt with the compound of Formula V

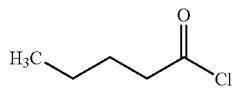

FORMULA V to obtain the compound of Formula VI, wherein the steps a) and b) are carried out at a temperature below about 40° C.

The compound of Formula III may be prepared by methods, for example, those known in the prior art, for example *Org. Process Res. Dev.*, 2007, 11(5) 892-898. The compound of Formula IV may be used as a free base or in the form of its salt, for example, the tosylate salt.

The reaction of the compound of Formula III and the compound of Formula IV or its salt may be carried out in the presence of a solvent system comprising water and one or more water-immiscible organic solvents. Examples of water-immiscible organic solvents include halogenated hydrocarbons, esters, ethers and mixtures thereof. Examples of halogenated hydrocarbons include dichloromethane, ethylene dichloride, chloroform and mixtures thereof. Examples of esters include ethyl acetate, isopropyl acetate and mixtures thereof. Examples of ethers include diethylether, diisopropylether and mixtures thereof. The solvent system can be, for example, a mixture of water and a halogenated hydrocarbon, for example, dichloromethane.

The reaction may be carried out in the presence of a base. The base may be an inorganic base. Examples of inorganic base include alkali metal carbonates, bicarbonates, hydroxides and mixtures thereof. Examples of alkali metal carbonates include lithium carbonate, sodium carbonate and potassium carbonate. Examples of alkali metal bicarbonates include sodium bicarbonate and potassium bicarbonate. Examples of alkali metal hydroxides include sodium hydroxide and potassium hydroxide. In some embodiments, potassium carbonate is used as the base.

The reaction may be carried out in the presence of a phase transfer catalyst. The phase transfer catalyst employed in the reaction of the compound of Formula III with the compound of Formula IV or its salt may be selected from, for example, tetrabutylammonium bromide, tetrapropylammonium bromide, tributylbenzylammonium chloride, tetraethylammonium bromide, tetraoctylammonium bromide, tetrabutylammonium hydrogen sulfate, benzyltrimethylammonium chloride, benzyltriethylammonium chloride, tetrabutylammonium acetate, tetrabutylammonium iodide, ethyltriphenylphosphonium bromide, and ethyltriphenylphosphonium iodide. In some embodiments, tetrabutylammonium bromide may be used as the phase transfer catalyst.

The reaction may be carried out at a temperature below about 40° C., for example, at about −20° to about 35° C. The reaction may be facilitated by stirring the reaction mixture for up to about 30 hours, for example, about 15 hours to about 25 hours. The compound of Formula II is obtained with a purity of about 98.0% or above, for example, with a purity of about 99.0% or above, or for example, with a purity of about 99.5% or above.

The compound of Formula II may be isolated as a free base or as a salt from the reaction mixture. The compound of Formula II may be isolated, for example, as an acid addition salt by treating the reaction mixture with an acid, for example, hydrochloric acid. The isolation of the compound of Formula II or its salts may be performed by the methods including layer separation, concentration, precipitation, filtration, decantation, distillation or a combination thereof.

The compound of Formula II or its salt is reacted with the compound of Formula V. The reaction may be carried out in the presence of a solvent system comprising water and one or more water-immiscible organic solvents. Examples of water-immiscible organic solvents include halogenated hydrocarbons, esters, ethers and mixtures thereof. Examples of halogenated hydrocarbons include dichloromethane, ethylene dichloride, chloroform and mixtures thereof. Examples of esters include ethyl acetate, isopropyl acetate and mixtures thereof. Examples of ethers include diethylether, diisopropylether and mixtures thereof. The solvent system can be, for example, a mixture of water and a halogenated hydrocarbon, for example, dichloromethane.

The reaction may be carried out in the presence of a base. The base may be an inorganic base. Examples of inorganic base include alkali metal carbonates, bicarbonates, hydroxides and mixtures thereof. Examples of alkali metal carbonates include lithium carbonate, sodium carbonate and potassium carbonate. Examples of alkali metal bicarbonates include sodium bicarbonate and potassium bicarbonate. Examples of alkali metal hydroxides include sodium hydroxide and potassium hydroxide. In some embodiments, potassium carbonate is used as the base.

The reaction may be carried out in the presence of a phase transfer catalyst. The phase transfer catalyst employed in the reaction of the compound of Formula II or its salt with the compound of Formula V may be selected from, for example, tetrabutylammonium bromide, tetrapropylammonium bromide, tributylbenzylammonium chloride, tetraethylammonium bromide, tetraoctylammonium bromide, tetrabutylammonium hydrogen sulfate, benzyltrimethylammonium chloride, benzyltriethylammonium chloride, tetrabutylammonium acetate, tetrabutylammonium iodide, ethyltriphenylphosphonium bromide, and ethyltriphenylphosphonium iodide. In some embodiments, tetrabutylammonium bromide may be used as the phase transfer catalyst.

The reaction may be carried out at a temperature range less than about 40° C., for example, at about −20° to about 35° C. For example, the reaction may be carried out at about −10° to about 5° C. The reaction may be facilitated by stirring the reaction mixture for up to about 30 hours, for example, about 30 minutes to about 5 hours.

The compound of Formula VI may be isolated from the reaction mixture or directly used in the subsequent steps of preparing valsartan without isolation. The isolation of the compound of Formula VI, if desired, may be carried out by the methods including layer separation, concentration, precipitation, filtration, decantation, distillation or a combination thereof.

The compound of Formula VI so obtained may be further converted into valsartan or its salts by methods, for example, those known in the prior art, for example, PCT Publication No. WO 05/049588, PCT Publication No. WO 05/049587, U.S. Patent Application Publication No. 2006/0281801 or U.S. Pat. No. 5,399,578. The conversion of the compound of Formula VI into valsartan or its salts may be carried out by reacting the compound of Formula VI with tributyltin halide and sodium azide to obtain benzyl protected valsartan of Formula IX, which is deprotected to obtain valsartan or its salts.

FORMULA IX

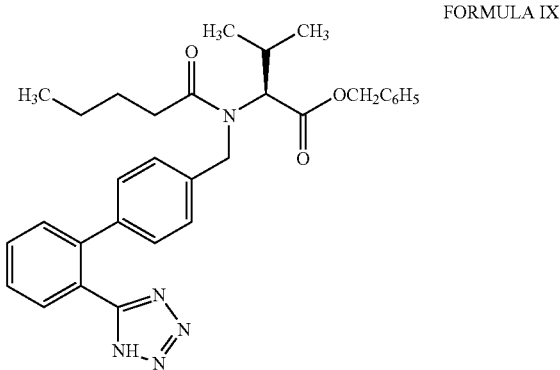

The reaction of the compound of Formula VI with tributyltin halide and sodium azide may be carried out in the presence of an organic solvent, for example, toluene or xylene. The reaction may be carried out at reflux temperature. The benzyl protected valsartan of Formula IX may be deprotected by hydrogenation with palladium-carbon in the presence of an organic solvent, for example, ethyl acetate, to obtain valsartan. The valsartan may be isolated as a salt, for example, as a barium salt by treating with barium hydroxide. The salt of valsartan may be further converted into valsartan by treating with an acid, for example, hydrochloric acid. The valsartan or its salt so obtained has a purity of about 99.0% or above, preferably about 99.9%.

In the following section embodiments are described by way of examples to illustrate the process of invention. However, these do not limit the scope of the present invention. Several variants of these examples would be evident to persons ordinarily skilled in the art.

EXAMPLES

Example 1

Preparation of (S)—N-[(2'-cyanobiphenyl-4-yl)methyl]-(L)-valine benzyl ester hydrochloride A mixture of potassium carbonate (152.2 g) and de-mineralized water (300 ml) was stirred for 10 to 15 minutes to dissolve the solid. The temperature of the mixture was maintained at 30° to 35° C. and dichloromethane (300 ml) was added. L-Valine benzyl ester tosylate (153.3 g), tetrabutyl ammonium bromide (10.0 g) and 4-bromomethyl-2'-cyanobiphenyl (100 g) were added to the reaction mixture. The reaction mixture was stirred for 20 to 24 hours at 30° to 35° C. After completion of the reaction de-mineralized water (400 ml) was added and the mixture was stirred for 5 minutes. The two phases were separated and the aqueous layer was extracted with dichloromethane (200 ml). The combined organic layer was washed with de-mineralized water (300 ml) and concentrated at 40° to 45° C. Ethyl acetate (600 ml) was then added to the residue and stirred for 5 to 10 minutes to dissolve the residue. The reaction mixture was cooled to 0° to 5° C. and concentrated hydrochloric acid (50 ml) was added to the reaction mixture. The mixture was stirred for 1 hour. The precipitated solid was filtered, washed with ethyl acetate and dried to obtain the title compound.

Yield: 140 g
Purity: 99.6% (by HPLC)

Example 2

Preparation of (S)—N-[(2'-cyanobiphenyl-4-yl)methyl]-N-valeroyl-(L)-valine benzyl ester A mixture of potassium carbonate (95.3 g) and de-mineralized water (100 ml) was stirred for 10 to 15 minutes to dissolve the solid. The temperature of the mixture was maintained at 25° to 30° C. and dichloromethane (300 ml) was added to the mixture. (S)—N-[(2'-Cyanobiphenyl-4-yl)methyl]-(L)-valine benzyl ester hydrochloride (100 g) and tetrabutyl ammonium bromide (10.0 g) were added to the mixture. The reaction mixture was cooled to −10° to −8° C. and valeryl chloride (36.1 g) was added at −10° to −5° C. The reaction mixture was stirred for 60 to 90 minutes at 0° to 5° C. After the completion of the reaction, the temperature was raised to 25° to 30° C. De-mineralized water (200 ml) was added to the reaction mixture and the mixture was stirred for 1 hour at 25° to 30° C. The two phases were separated and the organic layer was washed with de-mineralized water (200 ml). The organic layer was concentrated at 40° to 45° C. to obtain a residual liquid containing the title compound.

Example 3

Preparation of (S)—N-(1-benzyloxycarbonyl-2-methyl-prop-1-yl)-N-pentanoyl-N-[2'(1H-tetrazol-5-yl)biphenyl-4-yl-methyl]amine A mixture of (S)—N-[(2'-cyanobiphenyl-4-yl)methyl]-N-valeroyl-(L)-valine benzyl ester as obtained in Example 2, tributyltin chloride (150 g), sodium azide (30 g) and tetrabutyl ammonium bromide (10 g) in toluene (200 ml) was refluxed for 30 hours. After the completion of the reaction, the reaction mixture was cooled and stirred with a solution of toluene (200 ml), de-mineralized water (400 ml) and acetic acid (60 ml) for 1 hour. The organic layer was separated, concentrated and dissolved in 1,4-dioxane (500 ml). The solution was cooled to 10° to 15° C. and stirred with a solution of sodium hydroxide (27.6 g in 690 ml of water) at 0° to 5° C. for 1 hour. The aqueous layer was extracted twice with diisopropylether, acidified and extracted with ethyl acetate. The ethyl acetate layer was concentrated at reduced pressure to obtain title compound as oil.

Example 4

Preparation of (S)—N-(1-carboxy-2-methyl-prop-1-yl)-N-pentanoyl-N-[2'(1H-tetrazol-5-yl)biphenyl-4-yl-methyl]amine barium salt (Valsartan barium)

A solution of (S)—N-(1-benzyloxycarbonyl-2-methyl-prop-1-yl)-N-pentanoyl-N-[2'(1H-tetrazol-5-yl)biphenyl-4-yl-methyl]amine, as obtained in Example 3, in ethyl acetate was hydrogenated with palladium-carbon (10 g) at 50° to 55° C. for 8 hours. After the completion of the reaction, the reaction mixture was filtered, concentrated and dissolved in acetone (800 ml). The solution was treated with aqueous barium hydroxide solution (72.6 g) at 15° to 35° C. and stirred at 0° to 5° C. for 5 hours. The solid obtained was filtered, washed with acetone and dried to obtain the title compound as a white crystalline solid.

Yield: 105 g
HPLC Purity: 99.9%

Example 5

Preparation of (S)—N-(1-carboxy-2-methyl-prop-1-yl)-N-pentanoyl-N-[2'(1H-tetrazol-5-yl)biphenyl-4-yl-methyl]amine (Valsartan)

A slurry of valsartan barium (90 g) in ethyl acetate (900 ml) and water (360 ml) was treated with hydrochloric acid to attain a pH of about 2 to 2.5. The organic layer was separated, washed with water (3×270 ml) and concentrated at about 45° to 50° C. under reduced pressure. The residue was dissolved in ethyl acetate (225 ml) at 45° to 50° C., filtered at hot condition and cooled to 20° to 25° C. Pentane (900 ml) was then added slowly to the mixture and stirred for 1 hour at 20° to 25° C. The solid obtained was filtered, washed with pentane (2×90 ml) and dried under reduced pressure to obtain the title compound.

Yield: 60 g
Assay: 100.4%
Chiral purity: 99.9%
HPLC purity: 99.9%

We claim:

1. A process for preparing the compound of Formula VI

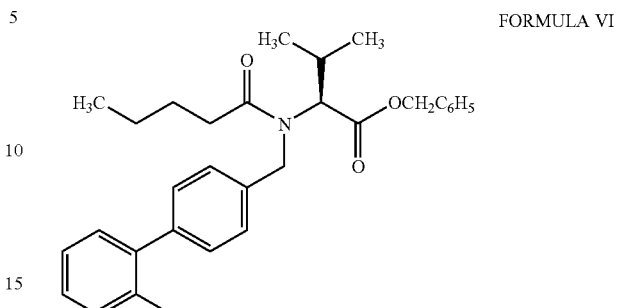

FORMULA VI comprising reacting the compound of Formula II or its salt

FORMULA II with the compound of Formula V

FORMULA V in the presence of a phase transfer catalyst.

2. A process according to claim 1 wherein the reaction is carried out in the presence of a solvent system comprising of water and one or more water immiscible organic solvents.

3. A process according to claim 2 wherein the water immiscible organic solvent is a halogenated hydrocarbon, ester, ether or mixtures thereof.

4. A process according to claim 3 wherein the water immiscible organic solvent is a halogenated hydrocarbon.

5. A process according to claim 4 wherein the halogenated hydrocarbon is dichloromethane.

6. A process according to claim 1 wherein the phase transfer catalyst is selected from the group consisting of tetrabutylammonium bromide, tetrapropylammonium bromide, tributylbenzylammonium chloride, tetraethylammonium bromide, tetraoctylammonium bromide, tetrabutylammonium hydrogen sulfate, benzyltrimethylammonium chloride, benzyltriethylammonium chloride, tetrabutylammonium acetate, tetrabutylammonium iodide, ethyltriphenylphosphonium bromide and ethyltriphenylphosphonium iodide.

7. A process according to claim 6 wherein the phase transfer catalyst is tetrabutylammonium bromide.

8. A process for preparing the compound of Formula VI

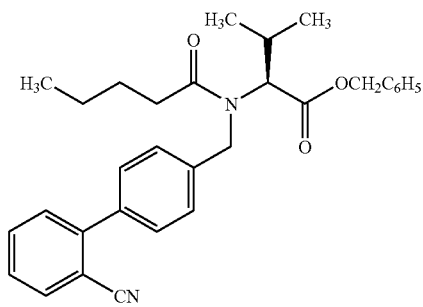

FORMULA VI comprising the steps of:
a) reacting the compound of Formula III

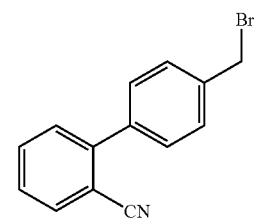

FORMULA III with the compound of Formula IV or its salt

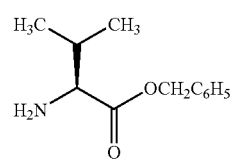

FORMULA IV in the presence of a phase transfer catalyst to obtain the compound of Formula II or its salt, and

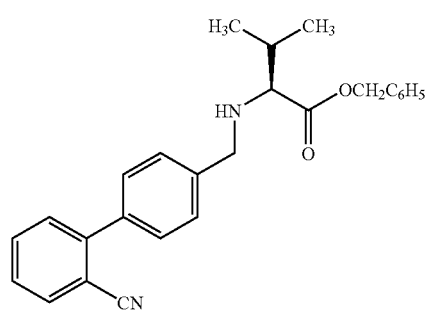

FORMULA II b) reacting the compound of Formula II or its salt with the compound of Formula V

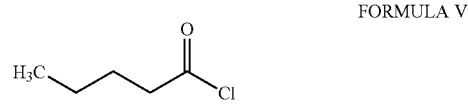

FORMULA V in the presence of a phase transfer catalyst to obtain the compound of Formula VI.

9. A process according to claim 8 wherein the phase transfer catalyst is selected from the group consisting of tetrabutylammonium bromide, tetrapropylammonium bromide, tributylbenzylammonium chloride, tetraethylammonium bromide, tetraoctylammonium bromide, tetrabutylammonium hydrogen sulfate, benzyltrimethylammonium chloride, benzyltriethylammonium chloride, tetrabutylammonium acetate, tetrabutylammonium iodide, ethyltriphenylphosphonium bromide and ethyltriphenylphosphonium iodide.

10. A process according to claim 9 wherein the phase transfer catalyst is tetrabutylammonium bromide.

11. A process for preparing the compound of Formula VI

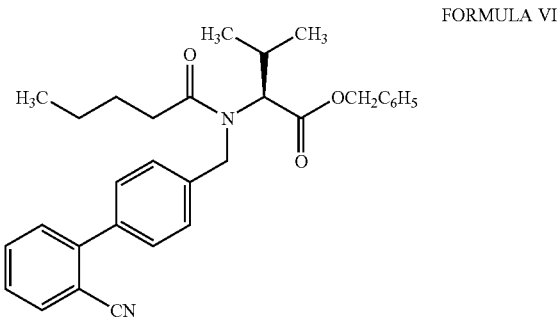

FORMULA VI comprising the steps of
a) reacting the compound of Formula III

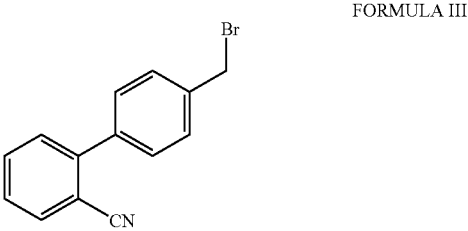

FORMULA III with the compound of Formula IV or its salt

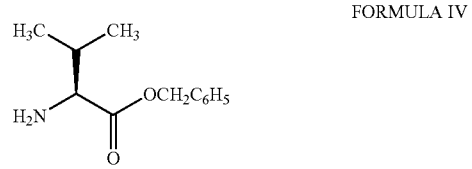

FORMULA IV to obtain the compound of Formula II or its salt, and

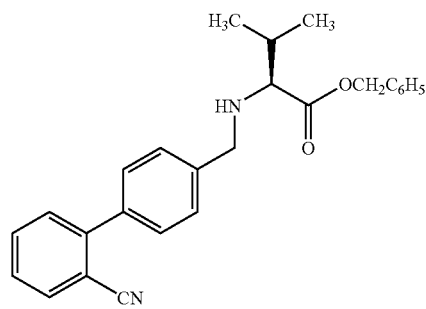

FORMULA II b) reacting the compound of Formula II or its salt with the compound of Formula V

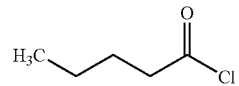

FORMULA V to obtain the compound of Formula VI, wherein the steps a) and b) are carried out at a temperature below about 40° C.

12. A process according to claim 11, wherein step a) is carried out at a temperature of about 20° to about 35° C.

13. A process according to claim 11, wherein step b) is carried out at a temperature of about −10° to about 5° C.

14. A process according to any one of claims 8, 9, 10, 11, 12 and 13, wherein the compound of Formula VI is converted into valsartan or its salts.

\* \* \* \* \*